United States Patent [19]

Isshiki et al.

[11] Patent Number: 4,978,778

[45] Date of Patent: Dec. 18, 1990

[54] PROCESS FOR PRODUCING VINYL ACETATE

[75] Inventors: Tomiya Isshiki, Tokyo; Yasuhiko Kijima, Chiba; Akiro Ito, Chiba; Yuh Miyauchi, Chiba; Takao Konko, Tokyo; Takayuki Watanabe, Chiba, all of Japan

[73] Assignee: Mitsubishi Gas Chemical Company, Inc., Tokyo, Japan

[21] Appl. No.: 560,279

[22] Filed: Dec. 13, 1983

Related U.S. Application Data

[63] Continuation of Ser. No. 301,409, Sep. 11, 1981, abandoned.

[30] Foreign Application Priority Data

Sep. 16, 1980 [JP] Japan .................. 55-128404
Oct. 3, 1980 [JP] Japan .................. 55-138411

[51] Int. Cl.$^5$ .................. C07C 67/00; C07C 69/15
[52] U.S. Cl. .................. 560/261; 560/248; 560/263; 560/265; 562/607; 562/608; 568/484; 568/492
[58] Field of Search .................. 560/261, 263

[56] References Cited

U.S. PATENT DOCUMENTS

| | | | |
|---|---|---|---|
| 2,021,698 | 11/1935 | Perkins | 260/106 |
| 2,425,389 | 8/1947 | Oxley et al. | 260/491 |
| 2,860,159 | 11/1958 | Sharp et al. | 260/491 |
| 3,579,566 | 5/1971 | Fenton | 560/263 |
| 4,189,441 | 2/1980 | Braca et al. | 560/232 |
| 4,221,918 | 9/1980 | Suzuki | 560/263 |
| 4,337,351 | 6/1982 | Larkins, Jr. | 560/263 |

FOREIGN PATENT DOCUMENTS

| | | |
|---|---|---|
| 1112555 | 5/1968 | United Kingdom . |
| 1538782 | 1/1979 | United Kingdom . |

OTHER PUBLICATIONS

Hydrocarbon Processing, vol. 44, No. 11, Nov. 1965, p. 287.
Pittman, Jr. et al., "Polymer-bound Catalysts and Reagents", Chemtech, Sep. 1973, pp. 560-566.
Michalska et al., "Supported Homogenous Catalysts", Chemtech, Feb. 1975, pp. 117-122.
Patent Abstracts of Japan, vol. 5, No. 75, May 19, 1981, p. 55.
Chemical Abstracts, 2726-2727, vol. 10, (1961).
Berichte, vol. 49, (1916), 1063-1071.

*Primary Examiner*—Vivian Garner
*Attorney, Agent, or Firm*—Fleit, Jacobson, Cohn, Price, Holman & Stern

[57] ABSTRACT

A process for producing vinyl acetate which comprises reacting acetic anhydride with hydrogen in the presence of a catalyst comprising
(a) a metal belonging to Group VIII of the Periodic Table or a compound of the metal, and
(b) (i) an acidic substance, or (ii) a halide
is disclosed.

16 Claims, 2 Drawing Sheets

PROCESS FOR PRODUCING VINYL ACETATE

This application is a continuation of application Ser. No. 301,409 filed Sept. 11, 1981, now abandoned.

BACKGROUND OF THE INVENTION

This invention relates to a process for producing vinyl acetate which comprises reacting acetic anhydride with hydrogen.

Vinyl acetate has been produced from acetylene in the past. Recently vinyl acetate has also been produced from ethylene. In case of producing vinyl acetate from ethylene, palladium chloride or mixture of palladium chloride and sodium acetate has been used as a catalyst.

In addition, process for producing vinyl acetate which comprises producing ethylidene diacetate (1,1-diacetoxy ethane) from acetaldehyde and acetic anhydride and causing thermal decomposition of the ethylidene diacetate to form vinyl acetate, and process for producing vinyl acetate and acetic acid from acetaldehyde and acetic anhydride directly have been proposed (refer to Hydrocarbon Process, 44 (11) 287 (1965), British Patent No. 1,112,555 and U.S. Pat. Nos. 2,021,698, 2,425,389 and 2,860,159).

SUMMARY OF THE INVENTION

The present inventors carried out research to find a process for effectively synthesizing vinyl acetate from acetic anhydride. As a result, we found a process for producing vinyl acetate by one stage by reacting acetic anhydride with hydrogen.

This invention relates to a process for producing vinyl acetate which comprises reacting acetic anhydride with hydrogen in the presence of a catalyst comprising (a) at least one material selected from the group consisting of metals belonging to Group VIII of the Periodic Table, compounds of the metals and mixtures thereof [sometimes hereinunder referred to as component (a)] and (b) (i) at least one acidic substance selected from the group consisting of protic acids, Lewis acids, solid acids and mixtures thereof [sometimes hereinunder referred to as component (b)(i)] or (ii) at least one halide selected from the group consisting of chlorides, bromides, iodides and mixtures thereof [sometimes hereinunder referred to as component (b)(ii)].

DETAILED EXPLANATION OF THE INVENTION

Figure 1:
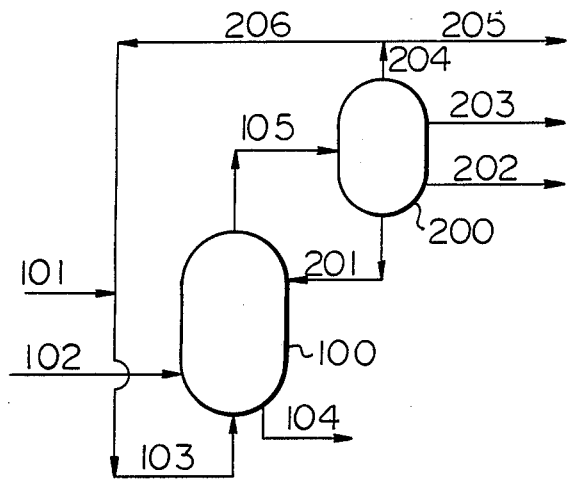
FIGS. 1-3 show flow sheets of the apparatus for carrying out this invention.

The mechanism of the reaction of acetic anhydride with hydrogen in this invention is not perfectly clear. However, it is believed that the reaction is expressed by the following equation:

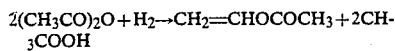

$$2(CH_3CO)_2O + H_2 \rightarrow CH_2=CHOCOCH_3 + 2CH_3COOH$$

The above reaction proceeds in a good state when a catalyst comprising (a) at least one material selected from the group consisting of metals belonging to Group VIII of the Periodic Table, compounds of the metals and mixtures thereof and (b) (i) at least one acidic substance selected from the group consisting of protic acids, Lewis acids, solid acids and mixtures thereof or (ii) at least one halide selected from the group consisting of chlorides, bromides, iodides and mixtures thereof is used.

The metals belonging to Group VIII of the Periodic Table can be used in any form of zero valence to higher valence state. For example, they can be used as metal itself or Raney metals, or finely divided particles of the metals, or as metal compounds, such as carbonates, oxides, peroxides, hydroxides, nitrates, sulfates, phosphates, halides, cyanides, thiocyanides, sulfonates, $C_1-C_5$ alkoxides, such as methoxides and ethoxides, phenoxide, carboxylates derived from $C_1-C_{20}$ alkanoic acids, oxyhalides, hydrides, carbonyls, nitrites, sulfites, phosphites, acetylacetonates and sulfides of metals or metal compounds coordinated with ammonia, cyanide, amines or amino acids.

The components (a) include, for example, metallic Pd, $PdX_2$, $PdX_2.2H_2O$, $PdX_2.2NH_3$, $Pd(CN)_2$, $Pd_2H$, $Pd(OH)_2$, $Pd(OH)_2.2NH_3$, $Pd(NO_3)_2$, $Pd_2O$, $PdO$, $PdO_2$, $PdSO_4.2H_2O$, $Pd_2S$, $[Pd(PPh_3)_2]Cl_2$, $PdS$, $PdS_2$, $Pd_3(PO_4)_2$, $Na_2PdX_4$, $Pd[(n-C_4H_9)_3P](CO)Cl_2$, $K_2PdX_4$, $Li_2PdX_4$, $Pd(OAc)_2$, $Pd(AcAc)_2$, $PdX_2(PhCN)_2$, $Pd(SCN)_2$, $Pd(NC)_2$, palladium benzene sulfonate, metallic Rh, $RhX_3$, $RhX_3.3H_2O$, $Rh(OH)_3$, $Rh(NO_3)_3.2H_2O$, $RhO$, $RhO_2$, $RhO_3$, $Rh_2(SO_4)_3.6H_2O$, $RhS$, $[Rh(AcO)_2]_2$, $Rh_2(CO)_3$, $Rh_6(CO)_{16}$, $RhCl(PPh_3)_3$, $[RhX(CO)_2]_2$, $Rh(AcAc)_3$, $Rh(SCN)_3$, $Rh(PPh_3)_2(CO)Cl_2$, $Rh(OPh)_3$, metallic Ir, $IrZ_3$, $IrX_3.H_2O$, $IrO_2$, $IrO_2.2H_2O$, $Ir_2O_3.3H_2O$, $IrS$, $Ir_2(CO)_8$, metallic Pt, $H_2PtX_6$, $PtX_2$, $PtX_4.Pt(OH)_2$, $Pt(OH)_4$, $PtO_2$, $PtO$, $Pt(PPh_3)_2(SnCl_3)_2$, $Pt_3O_4$, $Pt(CO)X_2$, $PtS$, $Pt_2S_3$, $Pt(CN)_2$, metallic Ru, $RuX_2$, $RuX_3$, $RuX_4$, $Ru(OH)_3$, $RuO_2$, $Ru_2O_3$, $Ru(NO_3)_36H_2O$, $Ru(CO)_2I_2$, $Ru(CO)_{12}$, metallic Os, $OsX_2$, $OsX_3$, $Os(CO)_4X_2$, $Os_3(CO)_{12}$, $Os(CO)_5$, metallic Fe, $FeS_2$, $FeX_2$, $Fe(NO_3)_2.6H_2O$, $FeSO_4.5H_2O$, $Fe(H_2PO_2)_3$, $FeSO_3$, $FeS_2O_3.5H_2O$, $Fe(NO_2)_2$, metallic Ni, $NiX_2$, $NiX_23H_2O$, $NiO$, $Ni_2O_3$, $Ni(CO)_4$, $NiCO_3$, $NiSO_4$, $NiS$, $Ni(CN)_2$, metallic Co, $Co_3O_4$, $CoX_3$, $Co(OAc)_2.4H_2O$, $CoCO_3$, $Co_2(SO_4)_3$, $CoSO_4$, wherein X is F, Cl, Br or I; Ph is phenyl group; AcO is acetoxy group and AcAc is acetylacetonate group.

The metal-polymer complexes in which a metal belonging to Group VIII of the Periodic Table is bonded to for example, silica, polyvinyl chloride, or polystyrene-divinylbenzene substrate crosslinked by phosphine, silyl, an amine, pyridine or sulfido bond can be used as component (a).

The metal-polymer complexes are disclosed in CHEMTECH, 1973 Pages 560-566 and CHEMTECH, 1975 pages 117-122.

Of these metals and metal compounds, palladium rhodium, platinum, ruthenium, osmium, cobalt and nickel and compounds of the metals are suitable; palladium, rhodium, platinum, ruthenium, cobalt and nickel and compounds of the metals are preferable; and palladium, rhodium, platinum and ruthenium and compounds of the metals are more preferable. Palladium or a palladium compound is most preferable. Of course, mixtures of metals belonging to Group VIII of the Periodic Table or compounds of the metals can also be used as component (a).

Component (a) constituting the catalyst may be soluble in a reaction solution. In this case a catalytic reaction is effected in a homogeneous system. The component (a) may also be insoluble in the reaction solution or partially soluble in the solution. In this case the reaction is effected in a heterogeneous system. The heterogeneous system catalysts include, for example, a metal itself, compounds of the metals or a metal supported on a carrier.

A metal can be supported on a carrier by coprecipitation, impregnation, blending, adsorption, and ion exchange and the like.

One of the processes for supporting a metal on a carrier is as follows: A carrier is impregnated with a solution of a metal belonging to Group VIII of the Periodic Table or a compound of the metal. The metal or the metal compound on the carrier is reduced with formalin, hydrogen, sodium formate, carbon monoxide, sodium borohydride, lithium aluminum hydride, or hydrazine, and then dried. Of course, the component (a) may be supported on a carrier by other methods.

Examples of the carriers include carbon, graphite, bone black, alumina, silica, silica alumina, barium sulfate, natural or synthetic zeolite, spinel, magnesia adhered alumina, thoria, titanium oxide, zirconium oxide, thorium oxide, lanthanum oxide, cerium oxide, zinc oxide, tantalum, clay, diatomaceous earth, Celite (trade name of product being commercially available from Johns-Manville Co.), asbestos, pumice stone, bauxite, terra abla, natural and treated terra abla, such as Super-Filtrol, silicon carbide, molecular sieves, ceramic honeycomb, boria, cements, alundum, corundum, brick, talc, gypsum and the like. Carbon, graphite, bone black, alumina, silica, silica alumina, barium sulfate, zeolite, spinel and magnesia adhered alumina are preferred. The carriers may be in the form of particles having uniform or ununiform size. The carriers may be in the form of molded articles, extruded articles, ceramic bars, balls, fragments, tiles and the like.

Heterogeneous system catalysts are preferable to homogeneous system catalysts, because separation and purification of the product, or separation or recovery of the catalyst are easy in a heterogeneous system.

Component (b)(i) or component (b)(ii) is necessary together with component (a).

Components (b)(i) mean materials serving as an acid in the reaction system. Components (b)(i) include protic acids, Lewis acids, or solid acids. Of acidic substances, materials acting as strong acid, such as, for example, strong protic acids or strong Lewis acids are preferable. Components (b)(i) have PKa below 5 and more suitably components (b)(i) have PKa below 3.

Examples of the acidic substances are shown in the following:

(I) Protic acid (A) inorganic acids and acid inorganic salts, such as HI, HBr, HCl, HF, $H_2SO_4$, $H_3PO_4$, $H_3BO_3$, $HClO_3$, $HBrO_3$, polyphosphoric acid, $FSO_3H$, $ClSO_3H$, $LiHSO_4$, $NaHSO_4$, $KHSO_4$, $PbHSO_4$, $CsHSO_4$, $LiH_2PO_4$, $KH_2PO_4$, $K_2HPO_4$, $RbH_2PO_4$, $Rb_2HPO_4$, $CsH_2PO_4$ and $Cs_2HPO_4$ (B) organic acids, such as
(a) methane sulfonic acid, trifluoromethane sulfonic acid, trichloroacetic acid, and trifluoroacetic acid,
(b) aromatic sulfonic acids, such as benzene sulfonic acid, toluene sulfonic acid, xylene sulfonic acid and naphthalene sulfonic acid.

In general, strong organic or inorganic protic acids as mentioned above or mixtures thereof can be used as an acidic substance. However, materials from which strong protic acids are formed in the reaction solution can also be used as an acidic substance.

(II) Lewis acids (A) Halides of metals belonging to Group IIa, IIIa, IVa, Va, VIa, IIIb, IVb, Vb, VIb, VIIb and VIII such as $BeX_2$, $MgX_2$, $BX_3$, $B_2X_4$, $AlX_3$, $GaX_2$, $GaX_3$, $InX$, $InX_2$, $InX_3$, $TlX$, $TlX_3$, $TlX_4$, $SiX_4$, $Si_2X_6$, $Si_3X_8$, $Si_4X_{10}$, $Si_5X_{12}$, $GeX$, $GeX_2$, $GeX_4$, $SnX_2$, $SnX_4$, $PX_3$, $PX_5$, $P_2X_4$, $AsX_3$, $AsX_5$, $SbX_3$, $SbX_5$, $BiX$, $BiX_2$, $BiX_3$, $TiX_2$, $TiX_3$, $TiX_4$, $ZrX_2$, $ZrX_3$, $ZrX_4$, $VX_2$, $VX_3$, $VX_4$, $CrX_2$, $CrX_3$, $MoX_2$, $MoX_3$, $MoX_4$, $MoX_5$, $WX_2$, $WX_4$, $WX_5$, $WX_6$, $MnX_2$, $MnX_3$, $MnX_4$, $ReX_3$, $ReX_4$, $ReX_5$, $ReX_6$, $FeX_2$, $FeX_3$, $CoX_2$, $CoX_3$, $CoX_4$, $NiX_2$, $RuX$, $RuX_2$, $RuX_3$, $RuX_4$, $CuX$, $CuX_2$, $AuX$, $AuX_2$, $AuX_3$, $ZnX_2$, $CdX_2$, $Hg_2X_2$, $HgX_2$, wherein X is F, Cl, Br or I. Of these Lewis acids, $MgCl_2$, $MgBr_2$, $MgI_2$, $BF_3$, $BCl_3$, $BBr_3$, $BI_3$, $AlCl_3$, $AlBr_3$, $AlI_3$, $SiCl_4$, $GeCl_4$, $SnCl_4$, $SnBr_4$, $SnI_4$, $SbF_5$, $SbCl_5$, $SbBr_3$, $SbCl_3$, $TiCl_4$, $TiBr_4$, $TiI_4$, $CrCl_3$, $CrBr_3$, $MoCl_5$, $WCl_6$, $FeCl_3$, $FeBr_3$, $FeI_3$, $CoCl_2$, $CoBr_2$, $NiCl_2$, $NiBr_2$, $NiI_2$, $CuCl$, $CuBr$, $CuCl_2$, $CuI$, $ZnCl_2$, $ZnBr_2$ and $ZnI_2$.

(B) Lewis type acids, such as $SO_3$, $SO_2$ and $B(CH_3)_3$.

(III) Solid acids (A) compounds, such as ZnO, $Al_2O_3$, $ThO_2$, $TiO_2$, $ZrO_2$, $CeO_2$, $As_2O_3$, $V_2O_3$, $Bi_2O_3$, $SiO_2$, $Cr_2O_3$, $MoO_2$, ZnS, CaS, $CaSO_4$, $MnSO_4$, $NiSO_4$, $CuSO_4$, $CoSO_4$, $CdSO_4$, $SrSO_4$, $ZnSO_4$, $MgSO_4$, $FeSO_4$, $BaSO_4$, $K_2SO_4$, $Al_2(SO_4)_3$, $Fe_2(SO_4)_3$, $Cr_2(SO_4)_3$, $Ca(NO_3)_2$, $Bi(NO_3)_2$, $Fe(NO_3)_3$, $BPO_4$, $FePO_4$, $CrPO_4$, $Ti_3(PO_4)_4$, $Zr_3(PO_4)_4$, $Cu_3(PO_4)_2$, $Ni_3(PO_4)_2$, $AlPO_4$, $Zn_3(PO_4)_2$ and $Mg(PO_4)_2$.

(B) compound oxides, such as $SiO_2$-$Al_2O_3$, $B_2O_3$-$Al_2O_3$, $Cr_2O_3$-$Al_2O_3$, $MoO_2$-$Al_2O_3$, $MoO_3$-$SiO_2$, $ZrO_2$-$SiO_2$, $Ga_2O_3$-$SiO_2$, $BeO$-$SiO_2$, $MgO$-$SiO_2$, $CaO$-$SiO_2$, $SrO$-$SiO_2$, $Y_2O_3$-$SiO_2$, $La_2O_3$-$SiO_2$, $SnO$-$SiO_2$, $PbO$-$SiO_2$, $MoO_3$-$Fe_2(MoO_4)_3$, $MgO$-$B_2O_3$, $TiO_2$-$ZnO$, $TiO_2$-$ZrO_2$, $TiO_2$-$SiO_2$, $TiO_2$-$SnO_2$, $TiO_2$-$WO_3$, $TiO_2$—$MoO_3$, $TiO_2$-$Sb_2O_3$, $TiO_2$-$Fe_2O_3$, $TiO_2$-$Cr_2O_3$, $TiO_2$-$V_2O_3$, $TiO_2$-$Mn_2O_3$, $TiO_2$-$Co_3O_4$, $TiO_2$-$NiO$, $TiO_2$-$CuO$, $TiO_2$-$Al_2O_3$, $TiO_2$-$Bi_2O_3$, $TiO_2$-$CdO$, $ZnO$-$Bi_2O_3$, $ZnO$-$As_2O_3$, $ZnO$-$Al_2O_3$, $ZnO$-$SiO_2$, $ZnO$-$ZrO_2$, $ZnO$-$Fe_2O_3$, $ZrO_2$-$ThO_2$, $Al_2O_3$-$NiO$, $Al_2O_3$-$Co_3O_4$, $Al_2O_3$-$CdO$, $Al_2O_3$-$Fe_2O_3$, $Al_2O_3$-$Bi_2O_3$, $Al_2O_3$-$ZrO_2$-$CdO$ and $TiO_2$-$MgO$.

(C) cation exchange resin or solidified acids in which p-toluene sulfonic acid, sulfuric acid, phosphoric acid, or boric acid is adhered to activated carbon, silica, quartz sand, alumina or diatomaceous earth.

Of acidic substances, acids (I) are preferable, and particularly, phosphoric acid, sulfuric acid, acid phosphates, acid sulfates methane sulfonic acid and aromatic sulfonic acids, such as benzene sulfonic acid, toluene sulfonic acid, xylene sulfonic acid and naphthalene sulfonic acid are more preferable; acid phosphates, acid sulfates and aromatic sulfonic acids, such as benzene sulfonic acid, toluene sulfonic acid and xylene sulfonic acid are most preferable. Halides, such as iodides, chlorides and/or bromides may be added to the reaction medium in the form of an alkyl halide, such as methyl iodide, an acid halogenide, such as acetyl iodide or hydrogen halide, such as hydrogen iodide as component (b)(ii). Materials which can convert to an alkyl halide, an acid halogenide or hydrogen halide can be used as a halide. Examples of the materials which can convert to an alkyl halide, an acid halogenide or a hydrogen halide by reacting with components in the reaction medium include inorganic halides, such as alkali metal halides, such as lithium halides, sodium halides, or potassium halides; alkaline earth metal halides, such as calcium halides or magnesium halides; metal halides, such as aluminum halides, zinc halides, copper halides, lanthanum halides, or cerium halides; halogens, such as chlorine, bromine or iodine; phosphrous halides, such as phosphorus trichloride, or phosphorus pentachloride and carbonyl halides, such as phosgene.

Of halides methyl chloride, methyl bromide and methyl iodide are more preferable from the viewpoint of corrosion resistance of reactor and separation of the reaction product from the reaction mixture and purification of the reaction product.

Amount of the component (a) employed depends on type of the catalyst employed, such as homogeneous system or heterogeneous system, and type of the reaction whether being effected in a fixed bed or fluidized bed. However, in general, the amount of the component (a) employed may be in the range of from $1 \times 10^{-4}$ to 25 wt %, preferably in the range of from $5 \times 10^{314}$ to 20 wt % more preferably from $1 \times 10^{-3}$ to 15 wt % and most preferably from $2.5 \times 10^{-3}$ to 10 wt. % on the basis of weight of a reaction solution in terms of metal.

Amount of the acidic substance employed is not critical. In general, amount of the acidic substance employed is in the range of $1 \times 10^{-2}$ to 20 wt %, preferably $1 \times 10^{-1}$ to 15 wt%, more preferably $2.5 \times 10^{-1}$ to 10 wt % and most preferably $5 \times 10^{-1}$ to 5 wt % on the basis of weight of a reaction solution.

Amount of halides employed as components (b) (ii) may be in the range of from $10^{-3}$ to 15 mol, preferably $10^{-2}$–5 mol and more preferably $10^{-1}$–3 mol per 1 liter of a reaction solution in terms of halogen atom.

The reaction of acetic anhydride with hydrogen of this invention sufficiently proceeds in the presence of the above mentioned catalyst. When halides (b) (ii) are used as component (b) constituting the catalyst, promoters may be used with the catalyst in order to increase the reaction rate and to enhance selectivity to the object product.

Examples of suitable promoters include metals having atomic weight of at least 6 and belonging to Groups Ia, IIa, IIIa, IVa, Va, Ib, IIb, Vb, VIb and VIIb of the Periodic Table and compounds of these metals. Preferable promoters include, for example metals having atomic weight of 210 or less and belonging to said Groups and compounds of the metals.

Metals which can be used as promoters include lithium, sodium, potassium, rubidium, cesium, beryllium, magnesium, calcium, strontium, barium, aluminum, indium, tin, lead, antimony, bismuth, copper, silver, zinc, cadmium, vanadium, chromium and manganese. Preferable metals include lithium, sodium, potassium, rubidium, cesium, magnesium, calcium, strontium, barium, aluminum, tin and antimony. More preferable metals include lithium, potassium rubidium, cesium, calcium, strontium, barium, tin and antimony. Most preferable metals include lithium, potassium, barium and antimony.

The promoters may be used in form of element, for example, finely divided particles of the metals. However, preferably, the promoters may be used in form of compound of the metals. Typical compounds of the metals include, for example, oxides, hydroxides, sulfides, halides, such as chlorides, fluorides, bromides or iodides, oxyhalides, hydrides, carbonyl, alkoxides, sulfates, sulfites nitrates, nitrites, phosphates, phosphites, chromates, molybdates, aliphatic, alicyclic and aromatic carboxylates, such as acetates, butyrates, decanates, laurates, stearates, succinates, adipates, benzoates and phthalates of the metals. Halide, such as chlorides, fluorides, bromides and iodides, sulfates, phosphates and carboxylates, such as acetates of the metals are more preferable. The promoter may be used alone or in form of mixture.

Use of the promoters is not critical. In general, amount of the promoter employed is in the range of from $1 \times 10^{-5}$ to 25% by weight, preferably $1 \times 10^{-4}$ to 20 % by weight, more preferably $1 \times 10^{-3}$ to 15% by weight and most preferably $2.5 \times 10^{-3}$ to 10% by weight on the basis of weight of a reaction solution.

In case of practicing this invention, the reaction temperature is not critical. In general, the reaction temperature may be in the range of 20° C.–500° C.

When component (b)(i) is used, the reaction temperature of 50°–250° C. is preferable, the reaction temperature of 80°–200° C. is more preferable, and the reaction temperature of 100°–180° C. is most preferable.

When component (b)(ii) is used, the reaction temporal of 30°–350° C. is preferable; the reaction temperature of 40°–250° C. is more preferable; and the reaction temperature of 80°–220° C. is most preferable.

The reaction pressure is kept high enough to keep the raw material(s), the solvent and the product in a liquid phase and to maintain appropriately partial pressure of hydrogen. The partial pressure of hydrogen may be in the range of 0.05-300 atm. preferably 0.1-200 atm. and more preferably 0.2-100 atm. However, partial pressure of hydrogen may be in the range of 0.01-500 atm.

Hydrogen used as a starting material need not necessarily have high purity. The hydrogen may contain carbon monoxide, carbon dioxide, methane, nitrogen, rare gases and the like. Synthesis gas mixture of hydrogen and carbon monoxide may be used as a raw material. Carbon monoxide contained in the hydrogen tends to make the catalyst stable and to restrain side reactions and consequently assists to allow the reaction to proceed effectively. In general, hydrogen containing more than 0.1 mol % of carbon monoxide may be used; hydrogen containing more than 1 mol % of carbon monoxide is preferable; and hydrogen containing more than 2 mol % of carbon monoxide is most preferable.

Acetic anhydride employed in the practice of this invention may be prepared via ketene (so-called Wacker process) from acetic acid which may be prepared by reaction of methanol and carbon monoxide. Alternatively acetic anhydride may be prepared from methyl acetate and carbon monoxide. For example, productions of acetic anhydride are disclosed in Japanese Patent Publication (Kokoku) No. 3926/1977, Japanese Patent Publication (Kokai) No. 65709/1976, and Japanese Patent Publication (Kokai) No. 59214/1979.

As mentioned above, acetic acid, methyl acetate and acetaldehyde may be incorporated in acetic anhydride employed as a raw material. However, incorporation of these compounds in acetic anhydride is permitted, as long as an overall balance of the process is obtained.

When acetic anhydride prepared by carbonylation reaction of methyl acetate is used as a starting material, the remainder of synthesis gas used in the carbonylation reaction may be used in the present invention.

Alternatively, the remainder of synthesis gas used in hydrogenation of the present invention may be used in the carbonylation reaction of methyl acetate.

A halide, such as methyl iodide is used as a co-catalyst in the above carbonylation reaction. The remainder of the halide used in the carbonylation reaction may be used as component (b)(ii) of this invention. In addition, the remainder of the halide as component (b)(ii) of this invention may be used as a co-catalyst in the carbonylation reaction.

In general, water may be incorporated into the reaction system. However, since commercially available hydrogen and acetic anhydride contains small amount of water, hydrogen and acetic anhydride containing water of such low concentration are permitted in this invention. The presence of water of more than 10 mol % on the basis of weight of a reaction solution is not preferable in this process, because such a large amount of water causes decomposition of the starting materials and the products.

In general, water content less than 5 mol % is preferable, and water content less than 3 mol % is more preferable. When raw materials contain large amount of water, they should be dried before introducing them into the reaction system.

Since acetic anhydride acts as a solvent for the reaction, another solvent is not necessarily used. As occasion demands, other solvents may be used. Use of proper solvent increases selectivity to vinyl acetate which is an object product.

Solvents which are usable for such purpose have electric constants of not more than 18 at room temperature. Organic solvents having dielectric constants of not more than 15 at 25° C. are preferable; organic solvents having dielectric constants of not more than 10 at 25° C. are more preferable; and organic solvents having dielectric constants of not more than 8 at 25° C. are most preferable.

In general, the organic solvents include aliphatic hydrocarbons having 5-20 carbon atoms, aromatic hydrocarbons having 6-20 carbon atoms, organic acid esters having 3-20 carbon atoms, ethers having 4-20 carbon atoms, ketones having 3-20 carbon atoms, alcohols having 4-20 carbon atoms and halogenated hydrocarbons having 1-20 carbon atoms. Of these solvents, saturated aliphatic hydrocarbons, aromatic hydrocarbons and organic acid esters are preferable.

Examples of the organic solvents include aliphatic hydrocarbons, such as pentane, hexane, heptane, octane, nonane, decane, undecane, dodecane, tridecane, tetradecane, pentadecane, hexadecane, cyclopentane, cyclohexane, and their alkylated derivatives; aromatic hydrocarbons, such as benzene, toluene, o-, p- and m-xylenes, trimethyl benzenes, ethyl benzene, propyl benzene, naphthalene, biphenyl, diphenyl methane, and their alkylated derivatives; organic acid esters, such as methyl acetate, ethyl acetate, propyl acetate, butyl acetate, amyl acetate, hexyl acetate, cyclohexyl acetate, octyl acetate, phenyl acetate, tolyl acetate, benzyl acetate, butyl formate, amyl formate, methyl propionate, ethyl propionate, methyl butyrate, ethyl butyrate, methyl benzoate, ethyl benzoate, methyl toluylate, dimethyl adipate, ethylene glycol diacetate, ethylidene diacetate, diethylene glycol diacetate, propylene glycol diacetate, γ-valerolactone, and δ-caprolactone; ethers, such as diethyl ether, dipropyl ether, methyl butyl ether, dibutyl ether, butyl ethyl ether, diamyl ether, diphenyl ether, anisole, tetrahydrofuran, 1,4-dioxane, butyl propyl ether, benzyl ethyl ether, phenetole, and dibenzyl ether; ketones, such as acetophenone, cyclohexanone, 3-pentanone and 4-methyl-2-pentanone; alcohols, such as 1-pentanol, 3-methyl-1-butanol, 3-methyl-2-propanol, 1-hexanol, 1-octanol, cyclohexanol, phenol and benzyl alcohol; halogenated hydrocarbons, such as methyl iodide, dichloro methane, chloroform, carbon tetrachloride, chlorobenzene dichlorobenzenes and iodobenzene. Mixtures of the above solvents may also be used.

Amount of the solvent employed is not critical. In general, amount of the solvent employed is in the range of 0 to 95 wt %, preferably 2 to 90 wt %, preferably 5 to 90 wt % and most preferably 5 to 80 wt % on the basis of weight of a reaction solution. It is preferable to select kind and amount of the solvent so that dielectric constant of the reaction solution amounts to less than 19, preferably less than 18 and more preferably less than 17 at 25° C.

The present process may be carried out by batch, semicontinuous or continuous method. When a heterogeneous system catalyst is used, the reaction can be effected in a fluidized bed or a fixed bed.

In the present invention, the reaction solution comprises acetic anhydride (starting material), a metal component, an acid substance or a halide, intermediates for reaction, ethylidene diacetate, vinyl acetate (object product) and acetic acid (by-product).

In order to increase amount of vinyl acetate formed, withdrawal of the resulting vinyl acetate from the reaction system is suitable. So, it is preferable to maintain concentration of vinyl acetate in the reaction system at less than 25 wt % by continuously withdrawing (for example distilling) the resulting vinyl acetate from the reaction system; it is more preferable to maintain the concentration at less than 15 wt %; and it is more preferable to maintain the concentration at less than 10 wt %; and it is most preferable to maintain the concentration at not more than 5 wt %.

It should be avoided that acetic acid, which is formed as a by-product, in large quantity remains in the reaction system. The reason is that acetic acid tends to prevent formation of the object product. So, in general, the concentration of acetic acid in the reaction system is maintained at less than 50 wt %, preferably less than 40 wt %, more preferably less than 30 wt % and most preferably less than 20 wt %.

Withdrawal of vinyl acetate and acetic acid from the reaction system is carried out, for example, by distillation.

According to this invention, vinyl acetate is directly produced from acetic anhydride and hydrogen. So, this invention does not need complicated process which comprises producing ethylidene diacetate from acetic anhydride and hydrogen, followed by forming vinyl acetate from the resulting ethylidene diacetate. In other words, this invention is more simple than the prior process; and according to this invention, separation of vinyl acetate is easier than that according to the prior process.

For better understanding of this invention, preferred embodiments of the invention are described hereunder by reference to the non-limiting accompanying drawings.

In FIG. 1, reaction zone 100 is composed of one or more pressure vessels of any type. Into the vessel are charged a suitable catalyst system typically consisting of a strong protic acid and a metal belonging to Group VIII of the Periodic Table or a compound of the metal and other liquid starting materials and, if necessary, a solvent. Pure hydrogen or mixture of hydrogen and other gases may be introduced under pressure at the bottom of vessel 100 with recycling gas 206 through line 103 and acetic anhydride is fed from line 102. The reaction mixture, namely materials containing the reaction products and unreacted raw materials are introduced from zone 100 through line 105 to separating zone 200 consisting of distilling units and one or more gas-liquid separating means. Gases containing hydrogen are separated in zone 200. Gases containing non-condensable hydrogen are recycled through lines 204 and 206 to vessel 100 with supply gas fed from line 101. As occasion demands, part of the gases is discharged outside from line 205. Vinyl acetate, acetaldehyde, acetic acid and acetic anhydride are separated by stripping and/or distillation in zone 200. Low boiling point components, such as unreacted materials, part of acetic acid and/or acetaldehyde are recycled into zone 100 through lines 204, 206 and 103. The object product, namely vinyl acetate and acetic acid as a by-product are condensed and separated from other components in zone 200 and discharged from lines 202 and 203. Acetic anhydride and ethylidene diacetate are recycled from line 201 to zone 100. As occasion demands, in order to prevent accumulation of high boiling point components, such as by-products or in order to withdraw part of the catalyst part of the reaction solution is discharged from line 104.

Figure 2:
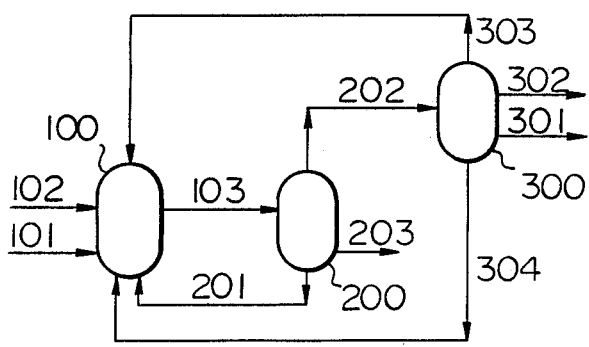

In FIG. 2, reaction zone 100 is composed of one or more pressure vessel of any type. Into the vessel are charged with a suitable catalyst system typically consisting of methyl iodide and a metal belonging to Group VIII of the Periodic Table or a compound of the metal and reaction solution. Raw material gas containing hydrogen is fed into bottom of zone 100 through line 101. Acetic anhydride is fed into zone 100 through line 102. Reaction products and unreacted materials are withdrawn through line 103, and fed into separating zone 200 consisting of one or more distilling units, for example, flashing means and/or fractionating columns. Nonvolatile catalyst and high boiling point components separated in zone 200 are recycled to zone 100 through line 201. Low boiling point components, such as acetaldehyde, methyl iodide, methyl acetate, vinyl acetate and acetic acid are fed through line 202 into separating zone 300 consisting of one or more distilling units. Acetaldehyde, methyl iodide and methyl acetate are recycled to zone 100 through line 303. Vinyl acetate and acetic acid separated in zone 300 are discharged together from lines 301 or 302, or are discharged separately from lines 301 and 302. Low boiling point components composed of acetaldehyde, methyl acetate and methyl iodide from zone 300 are recycled into zone 100 through line 303; and high boiling point components composed of acetic anhydride and ethylidene diacetate are recycled into zone 100 through line 304.

Figure 3:
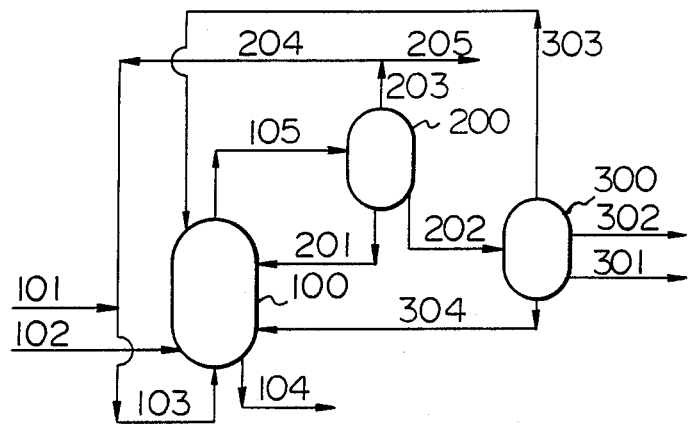

In FIG. 3, reaction zone 100 is composed of one or more pressure vessel of any type. Into the vessel are charged a suitable catalyst system typically consisting of methyl iodide and a metal belonging to Group VIII of the Periodic Table or a compound of the metal and reaction solution. Raw material gas is fed to bottom of zone 100 from line 101 through line 103 with recycled gas. Acetic anhydride is fed to zone 100 from line 102. The reaction products and unreacted materials are discharged from zone 100 from line 105 and fed to separating zone 200 consisting of one or more gas-liquid separating means and distilling units. Vapor of materials containing hydrogen is separated in zone 200. Gas containing non-condensable hydrogen is recycled to zone 100 through lines 203, 204 and 103 with supply gas from line 101. As occasion demands, part of the gas separated in zone 200 is discharged outside from line 205. Acetaldehyde, methyl iodide, methyl acetate, vinyl acetate and acetic acid are separated in zone 200 by stripping and/or by distillation. Part of acetic acid and of acetic anhydride and most of acetaldehyde, methyl iodide and methyl acetate are recycled to zone 100 with the gas containing hydrogen. Materials containing vinyl acetate and acetic acid separated in zone 200 are discharged from zone 200 to separating zone 300 through line 202. Low boiling point components, such as methyl acetate and methyl iodide are recycled from zone 300 to zone 100 through line 303. High boiling point components, such as acetic anhydride and ethylidene diacetate are recycled from zone 300 to zone 100 through line 304. Vinyl acetate (object product) and acetic acid (by-product) are discharged together from lines 301 or 302, or discharged separately from lines 301 and 302. As occasion demands, in order to prevent accumulation of polymers formed as by-products during the reaction and other high boiling point components or in order to withdraw part of the catalyst, part of the reaction solution is discharged from zone 100 through line 104.

The following examples are given as illustrative embodiment of the invention and should not be construed as limiting its scope. All parts and percents are on a weight basis, unless otherwise specified.

EXAMPLE 1

This example was carried out by using the apparatus as shown in FIG. 1. Into zone 100 including pressure reactor were filled reaction solution containing 1 mil mol of palladium acetate, and 20 milli mol of para-toluenesulfonic acid per 1 mol of acetic anhydride. Air in the vessel was purged with mixed gas of hydrogen and carbon monoxide (7:3 by volume). The temperature rose to 150° C. Thereafter, the mixed gas was fed to pressure of 5 kg/cm$^2$G and gas was recycled through zone 100, line 105, zone 200, lines 204, 206 and 103 at rate of 1.0 part of min. and at the same time acetic anhydride was continuously fed into zone 100 at rate of 0.6 parts per hour. Hydrogen gas was continuously fed into zone 100 from line 101 so that pressure of zone 100 was maintained at 5 kg/cm$^2$G. Mixture of vinylacetate and acetic anhydride were fed from zone 100 to separating zone 200 including distilling units and separated in zone 200. Vinyl acetate separated in zone was discharged at rate of 0.522 parts per hour from line 203 with acetic acid.

EXAMPLE 2

Into a pressure vessel were charged 1 mol of acetic anhydride, 1 milli mol of palladium acetate and 10 milli mol of sulfuric acid. Air in the vessel was purged with mixed gas of hydrogen and carbon monoxide (7:3 by volume). The mixed gas was fed to 25 Kg/cm$^2$G. The vessel was heated to 145° C. within a determined time. During heating, the mixed gas was continuously fed into the vessel so that the pressure of vessel is maintained at 25 Kg/cm$^2$G. After the reaction completed, the reaction mixture was cooled and was discharged. GC-Mass analysis showed that it contained vinyl acetate with acetic anhydride.

EXAMPLE 3

The procedure of Example 2 was repeated except that potassium hydrogensulfate was used in place of sulfuric acid. Similarly, formation of vinyl acetate was confirmed.

EXAMPLE 4

In an autoclave were charged 150g of acetic anhydride, 0.45 g of palladium black, and 2.0 g of potassium hydrogensulfate. Hydrogen was charged under pressure into the autoclave to pressure of 10 Kg/cm$^2$G. The temperature in the autoclave was raised to 175° C. The reaction was carried out for 30 minutes. GC analysis showed that the reaction mixture contained 0.421 g of vinyl acetate, 2.50 g of ethylidene diacetate and 1.49 g of acetaldehyde with considerable amount of acetic acid.

EXAMPLE 5

The procedure of Example 2 was repeated except that aluminum chloride was used in place of sulfuric acid. Similarly formation of vinyl acetate was confirmed.

EXAMPLE 6

This example was carried out by using the apparatus as shown in FIG. 1. Into zone 100 including pressure reactor was filled reaction solution containing 2 milli mol of rhodium acetate, and 20 milli mol of benzenesulfonic acid per 1 mol of acetic anhydride. Air in the vessel was purged with mixed gas of hydrogen and carbon monoxide (4:1 by volume). The temperature rose to 145° C. Thereafter, the mixed gas was fed from bottom of zone 100 to pressure of 10 Kg/cm$^2$G, and gas was recycled through zone 100, line 105, zone 200 and lines 204, 206 and 103 at rate of 1.4 part/minute, and at the same time acetic anhydride was continuously fed from line 102 into zone 100 at rate of 0.35 parts per hour. The gas was consumed and mixed solution of vinyl acetate, acetic acid and acetic anhydride was discharged from zone 100. Hydrogen gas was continuously fed into zone 100 from line 101 so that pressure of zone 100 was maintained at 10 Kg/cm$^2$G. Vinyl acetate and acetic acid were separated from the mixed solution in zone 200. Vinyl acetate was withdrawn with considerable amount of acetic acid from zone 200 at rate of 0.312 parts per hour through line 203.

EXAMPLE 7

This example was carried out by using the apparatus as shown in FIG. 1. Into zone 100 including pressure reactor was filled reaction solution containing 1.5 milli mol or ruthenium chloride, and 20 milli mol of benzenesulfonic acid per 1 mol of acetic anhydride. Air in the vessel was purged with mixed gas of hydrogen and carbon monoxide (4:1 by volume) The temperature rose to 140° C. Thereafter, the mixed gas was fed from bottom of zone 100 to pressure of 10 Kg/cm$^2$G, and gas was recycled through zone 100, line 105, zone 200 and lines 204, 206 and 103 at rate of 0.64 part/minute, and at the same time acetic anhydride was continuously fed into zone 100 at rate of 0.15 parts per hours. The gas was consumed and mixed solution of vinyl acetic acid and acetic anhydride was discharged from zone 100. Hydrogen gas was continuously fed into zone 100 from line 101 so that pressure of zone 100 was maintained at 10 Kg/cm$^2$G. Vinyl acetate and acetic acid were separated from the mixed solution in zone 200. Vinyl acetate was withdrawn with considerable amount of acetic acid from zone 200 at rate of 0.125 parts per hour through line 203.

EXAMPLE 8

This example was carried out by using the apparatus as shown in FIG. 1. Into zone 100 including pressure reactor was filled reaction solution containing 2.04 g of palladium (5%) supported on activated carton (being commercially available from Nippon Engelhard) and 20 milli mol of para-toluenesulfonic acid per 1 mol of acetic anhydride. Air in the vessel was purged with mixed gas of hydrogen and carbon monoxide (4:1 by volume). The temperature rose to 145° C. Thereafter, the mixed gas was fed from bottom of zone 100 to pressure of 5 Kg/cm$^2$G, and gas was recycled through zone 100, line 105, zone 200 and lines 204, 206 and 103 at rate of 1.0 part/minute, and at the same time acetic anhydride was continuously fed into zone 100 at rate of 0.5 parts per hour. The gas was consumed and mixed solution of vinyl acetate, acetic acid and acetic anhydride was discharged from zone 100. Hydrogen gas was continuously fed into zone 100 from line 101 so that pressure of zone 100 was maintained at 5 Kg/cm$^2$G. Vinyl acetate and acetic acid were separated from the mixed solution in zone 200. Vinyl acetate was withdrawn with considerable amount of acetic acid from zone 200 at rate of 0.460 parts per hour through line 203.

EXAMPLE 9

Into an autoclave were charged 100 g of acetic anhydride, 35 g of methyl acetate, 15 g of methyl iodide and 4.5 g of palladium (5%) supported on activated carbon (being commercially available from Nippon Engelhard). Mixed gas of hydrogen and carbon monoxide (2:1 by volume) was charged into the autoclave to pressure of 30 Kg/cm$^2$G. The temperature in the autoclave was raised to 175° C. At that temperature, hydrogen was fed so as to maintain the pressure at 50 Kg/cm$^2$G with stirring for 30 minutes. After cooling the reaction mixture, GC analysis showed that it contained 2.33 g of vinyl acetate, 20.6 g of ethylidene diacetate, 0.331 g of acetaldehyde and 0.109 g of ethyl acetate. The remainder components were considerable amount of acetic acid, unreacted acetic anhydride, methyl acetate and methyl iodide.

EXAMPLE 10

Into an autoclave were charged 135 g of acetic anhydride, 5 g of methyl iodide and 4.5 g of palladium (5 %) supported on activated carbon (sold as PM Type from Kawaken Finechemical Co.). The reaction was effected for 30 minutes while feeding mixed gas of hydrogen and carbon monoxide (2:1 by volume) into the autoclave so as to maintain the pressure at 50 Kg/cm$^2$G. GC analysis showed that the reaction mixture contained 0.778 g of vinyl acetate, 88.0 g of ethylidene diacetate and 1.27 g of acetaldehyde.

EXAMPLE 11

Into an autoclave were charged 135 g of acetic anhydride, 15 g of methyl iodide, 4.5 g of palladium (5 %) supported on activated carbon and 5.0 g of lithium acetate. The reaction was carried out at 175° C. for 30 minutes while feeding mixed gas of hydrogen and carbon monoxide (2:1 by volume) into the autoclave so as to maintain the pressure at 50 Kg/cm$^2$G. GC analysis showed that the reaction mixture contained 1.43 g of vinyl acetate and 18.4 g of ethylidene diacetate with considerable amount of acetic acid.

EXAMPLE 12

The procedure of Example 9 was repeated except that hydrogen was used in place of fixed gas of hydrogen and carbon monoxide. GC analysis showed that the reaction mixture contained 2.58 g of vinyl acetate, 22.9 g of ethylidene diacetate and 0.288 g of acetaldehyde.

EXAMPLE 13

Into an autoclave were charged 35 g of acetic anhydride, 100 g of methyl acetate, 15 g of methyl iodide and 2.25 g of palladium (5%) supported on activated carbon (Nippon Engelhard). The reaction was effected for 50 minutes in the same way as in Example 9. GC analysis showed that 0.861 g of vinyl acetate, 3.77 g of ethylidene diacetate, 2.51 g of acetaldehyde and 0.135 g of ethyl acetate were formed with considerable amount of acetic acid.

EXAMPLE 14

Into an autoclave were charged 135 g of acetic anhydride, 15 g of methyl iodide and 4.5 g of palladium (5%) supported on barium sulfate (Kawaken Finechemical Co.). The reaction was effected for 90 minutes in the same way as in Example 9. GC analysis showed that 0.415 g of vinyl acetate and 14.0 g of ethylidene diacetate were formed with considerable amount of acetic acid.

EXAMPLE 15

The procedure of Example 9 was repeated except that 0.475 g of palladium acetate was used in place of palladium supported on activated carbon and the reaction was effected for 3 hours. GC analysis showed that 1.70 g of vinyl acetate, 35.3 g of ethylidene diacetate, 0.738 g of acetaldehyde and 0.141 g of ethyl acetate were formed with considerable amount of acetic acid.

EXAMPLE 16

The procedure of Example 9 was repeated except that 0.451 g of palladium chloride was used in place of palladium supported on activated carbon and the reaction was effected for 3 hours. GC analysis showed that 1.51 g of vinyl acetate and 32.1 g of ethylidene diacetate were formed with considerable amount of acetic acid.

EXAMPLE 17

The procedure of Example 9 was repeated except that 0.225 g of palladium black being commercially available from Nippon Engelhard was used in place of palladium (5%) supported on activated carbon. GC analysis showed that 1.74 g of vinyl acetate, 15.8 g of ethylidene diacetate, 0.090 g of ethyl acetate and 0.251 g of acetaldehyde were formed with considerable amount of acetic acid.

EXAMPLE 18

Into an autoclave were charged 100 g of acetic anhydride, 35 g of methyl acetate, 15 g of methyl iodide and 4.5 g of rhodium (5%) supported on activated carbon. Mixed gas of hydrogen and carbon monoxide (3:1 by volume) was fed into the autoclave to pressure of 50 Kg/cm$^2$G. The temperature was raised to 175° C. Thereafter, the reaction was effected at 50 Kg/cm$^2$G and 175° C. with stirring. After cooling the reaction mixture, GC analysis showed that it contained vinyl acetate with considerable amount of acetic acid and 14.2 g of ethylidene diacetate.

EXAMPLE 19

The procedure of Example 17 was repeated except that 4.5 g of platinum (5%) supported on activated carbon was used in place of palladium supported on activated carbon. GC analysis showed that vinyl acetate was formed with considerable amount of acetic acid and 8.28 g of ethylidene diacetate.

EXAMPLE 20

The procedure of Example 17 was repeated except that 4.5 g of ruthenium (5%) supported on activated carbon was used in place of palladium supported on activated carbon. GC analysis showed that vinyl acetate was formed with considerable amount of acetic acid and 15.5 g of ethylidene diacetate.

EXAMPLE 21

The procedure of Example 9 was repeated except that 10 g of methyl chloride was used in place of methyl iodide and the reaction was effected for 6 hours. GC analysis showed that 0.116 g of vinyl acetate, and 43.3 g of ethylidene diacetate were formed with considerable amount of acetic acid.

EXAMPLE 22

The procedure of Example 9 was repeated except that 10 g of methyl bromide was used in place of methyl iodide and the reaction was effected for 6 hours. GC analysis showed that 0.212 g of vinyl acetate and 65.8 g of ethylidene diacetate were formed with considerable amount of acetic acid.

EXAMPLE 23

The procedure of Example 9 was repeated except that 10 g of calcium iodide was used in place of methyl iodide and the reaction was carried out for 6 hours. GC analysis showed that 0.083 g of vinyl acetate and 12.7 g of ethylidene diacetate were formed with considerable amount of acetic acid.

EXAMPLE 24

Into an autoclave were charged 40 g of acetic anhydride, 20 g of methyl acetate, 15 g of methyl iodide, 75 g of ethylidene diacetate, 4.5 g of palladium (5%) supported on activated carbon (Nippon Engelhard). The reaction was carried out for 4 hours at 175° C. and at 50 Kg/cm$^2$G by using mixed gas of carbon monoxide and hydrogen (2:1 by volume). After cooling the reaction mixture, GC analysis showed that it contained 7.71 g of vinyl acetate, and 87.6 g of ethylidene diacetate.

EXAMPLE 25

Into an autoclave were charged 135 g of acetic anhydride, 15 g of methyl iodide, 0.45 g of palladium black and 2.0 g of potassium fluoride. The reaction was carried out for 30 minutes at 175° C. while maintaining the pressure in the autoclave at 10 Kg/cm$^2$G by using hydrogen. After the reaction completed, GC analysis showed that the reaction mixture contained 1.14 g of vinyl acetate and 4.92 g of ethylidene diacetate with considerable amount of acetic acid.

EXAMPLE 26

The procedure of Example 25 was repeated except that 2.0 g of potassium chloride was used in place of potassium fluoride. GC analysis showed that the reaction mixture contained 1.52 g of vinyl acetate, 4.04 g of ethylidene diacetate and 0.364 g of acetaldehyde with considerable amount of acetic acid.

EXAMPLE 27

The procedure of Example 25 was repeated except that 2.0 g of potassium bromide was used in place of potassium fluoride. GC analysis showed that the reaction mixture contained 1.26 g of vinyl acetate and 3.67 g of ethylidene diacetate with considerable amount of acetic acid.

EXAMPLE 28

The procedure of Example 25 was repeated except that 2.0 g of potassium iodide was used in place of potassium fluoride. GC analysis showed that the reaction mixture contained 0.873 g of vinyl acetate and 2.25 g of ethylidene diacetate with considerable amount of acetic acid.

EXAMPLE 29

The procedure of Example 25 was repeated except that 2.0 g of potassium sulfate was used in place of potassium fluoride. GC analysis showed that the reaction mixture contained 1.72 g of vinyl acetate, 5.69 g of ethylidene diacetate and 0.026 g of acetaldehyde with considerable amount of acetic acid.

EXAMPLE 30

The procedure of Example 25 was repeated except that 2.0 g of potassium dihydrogenphosphate was used in place of potassium fluoride. GC analysis showed that the reaction mixture contained 2.35 g of vinyl acetate, 9.14 g of ethylidene diacetate and 0.502 g of acetaldehyde with considerable amount of acetic acid.

EXAMPLE 31

The procedure of Example 25 was repeated except that 2.0 g of potassium acetate was used in place of potassium fluoride. GC analysis showed that the reaction mixture contained 1.38 g of vinyl acetate and 5.63 g of ethylidene diacetate with considerable amount of acetic acid.

EXAMPLE 32

Into an autoclave were charged 100 g of acetic anhydride, 35 g of benzene, 15 g of methyl iodide, and 0.45 g of palladium black (Nippon Engelhard). Air in the autoclave was purged with nitrogen. The temperature in the autoclave was raised to 175° C., and then hydrogen was fed under pressure into the autoclave to 10 Kg/cm$^2$G. The reaction was carried out for 30 minutes at 175° C. with stirring while maintaining the pressure in the autoclave at 10 Kg/cm$^2$G by feeding hydrogen into the autoclave. After cooling the reaction mixture, GC analysis showed that 2.06 g of vinyl acetate, 14.6 g of ethylidene diacetate and 0.360 g of acetaldehyde were formed. Other components were considerable amount of acetic acid.

EXAMPLES 33–38

The procedures of Example 32 were repeated except that 35 g of each of solvents in shown in Table 1 was used in place of benzene. The results are shown in Table 1.

TABLE 1

|  | Solvent | Ex. 33 n-heptane | Ex. 34 n-amyl acetate | Ex. 35 n-octyl acetate | Ex. 36 phenyl acetate | Ex. 37 benzyl acetate | Ex. 38 methyl isobutyl ketone |
|---|---|---|---|---|---|---|---|
| Product (g) | vinyl acetate | 1.01 | 1.43 | 1.68 | 2.27 | 1.81 | 1.39 |
|  | ethylidene diacetate | 4.44 | 11.3 | 14.1 | 26.4 | 23.4 | 23.5 |
|  | acetaldehyde | 1.17 | 0.502 | 0.393 | 0.140 | 0.035 | — |

EXAMPLE 39

The procedure of Example 32 was repeated except that 70 g of benzene was used and 65 g of acetic anhydride was used. After the reaction completed, 0.929 g of vinyl acetate, 2.14 g of ethylidene diacetate and 1.57 g of acetaldehyde were formed.

EXAMPLE 40

Into an autoclave were charged 90 g of acetic anhydride 45 g of ethylidene diacetate, 15 g of methyl iodide, 0.45 g of palladium black and 2.0 g of potassium acetate. The reaction was carried out for 30 minutes at 175° C. while maintaining the pressure in the autoclave at 10 Kg/cm$^2$G by using hydrogen. After the reaction completed, GC analysis showed that the reaction mixture contained 2.29 g of vinyl acetate 49.2 g of ethylidene diacetate and 0.094 g of acetaldehyde with considerable amount of acetic acid.

EXAMPLE 41

The procedure of Example 40 was repeated except that 4.5 g of lithium iodide was used in place of potassium acetate. After the reaction completed, GC analysis showed that 1.74 g of vinyl acetate, 45.6 g of ethylidene diacetate and 0.024 g of acetaldehyde with considerable amount of acetic acid.

EXAMPLE 42

This example was carried out by using the apparatus as shown in FIG. 2. Into zone 100 was charged mixture of 35 wt % of acetic anhydride, 10 wt % of methyl acetate, 10 wt % of methyl iodide, 42 wt % of ethylidene diacetate and 3 wt % of palladium (5%) supported on activated carbon in determined amount. Air in zone 100 was purged with mixed gas of hydrogen and carbon monoxide (2:1 by volume). The temperature in the vessel was raised to 175° C. The mixed gas was fed through line 101 from bottom of zone 100 under pressure to 30 Kg/cm$^2$G. The mixture was stirred for 3 hours while maintaining the pressure at 30 Kg/cm$^2$G by feeding hydrogen into the vessel from line 101. Thereafter, movement of the solution started so that average residence time of the solution amounted to 3 hours, and at the same time acetic anhydride was fed into zone 100 from line 102 at rate of 13.8 g/hour, and hydrogen was continuously fed into zone 100 so as to maintain the pressure at 30 Kg/cm$^2$G. The reaction mixture withdrawn from line 103 was fed into separating zone 200 and flash-distilled there to obtain low boiling point components containing 5.22 wt % of vinyl acetate. The low boiling point components were fed into separating zone 300 including distilling units through line 202. High boiling point components and the catalyst separated in zone 200 were recycled into zone 100 through line 201. The components charged into zone 300 were separated, the low boiling point components mainly composed of methyl acetate and methyl iodide were recycled into zone 100 through line 303, and high boiling point components mainly composed of acetic anhydride and ethylidene diacetate were recycled into zone 100 through line 304. Vinyl acetate (object product) was discharged from zone 300 through line 302 at rate of 5.47 g/hour and acetic acid was discharged from zone 300 through 301 at rate of 8.11 g/hour.

EXAMPLE 43

This example was carried out by using the apparatus as shown in FIG. 3. Mixture of 35 wt % of acetic anhydride, 10 wt % of methyl acetate, 10 wt % of methyl iodide, 42 wt % of ethylidene diacetate and 3 wt % of palladium (5%) supported on activated carbon in a determined amount was charged into zone 100. Air in zone 100 was purged with mixed gas of hydrogen and carbon monoxide (3:1 by volume). The temperature in the zone was raised to 175° C. The mixed gas was fed from bottom of zone 100 under pressure to 30 Kg/cm$^2$G. The mixture was stirred for 3 hours while maintaining the pressure at 30 Kg/cm$^2$G by feeding hydrogen into zone 100 through line 101. Thereafter, movement of the solution started so that average residence time of the solution amounted to 3 hours, and at the same time acetic anhydride was fed into zone 100 from line 102 at rate of 14.7 g/hour, and hydrogen was continuously fed into zone 100 so as to maintain the pressure at 30 Kg/cm$^2$G, and gas was circulated through zone 100, line 105, separating zone 200 including distilling units, and lines 203, 204 and 103. Components containing 6.8 wt % of vinyl acetate condensed at 100° C. in zone 200 were fed into separating 300 including fractionating means through line 202. Low boiling point components mainly composed of methyl acetate and methyl iodide, which were separated in zone 300 were recycled into zone 100 through line 303, and high boiling point components mainly composed of acetic anhydride and ethylidene diacetate, which were separated in zone 300 were recycled into zone 100 through line 304. Vinyl acetate (object product) was discharged charged from zone 300 through line 302 at rate of 5.76 g/hour. Acetic acid was discharged from zone 300 through line 301 at rate of 8.61 g/hour.

What is claimed is:
1. A process for producing vinyl acetate which comprises reacting acetic anhydride with hydrogen gas in the presence of a catalyst consisting essentially of
   (a) at least one material selected from the group consisting of metals belonging to Group VIII of the Periodic Table, compounds of the metals and mixtures thereof and
   (b) at least one material selected from the group consisting of alkyl chlorides, alkyl bromides, alkyl iodides and mixtures thereof and materials convertible to an alkyl halide while removing vinyl acetate from the reaction system.

2. The process as defined in claim 1 wherein said component (a) constituting the catalyst is selected from the group consisting of palladium, rhodium, platinum, ruthenium, osmium, cobalt, nickel and compounds of these metals.

3. The process as defined in claim 1 wherein the amount of the component (a) employed is in the range of from $1 \times 10^{-4}$ to 25 wt % on the basis of weight of a reaction solution in terms of metal.

4. The process as defined in claim 1 wherein the reaction is carried out in the presence of a solvent, said solvent being organic material having a dielectric constant of not more than 18 at 25° C.

5. The process as defined in claim 4 wherein the solvent is selected from the group consisting of aliphatic hydrocarbons, aromatic hydrocarbons, organic acid esters, ethers, ketones, alcohols, and halogenated hydrocarbons.

6. The process as defined in claim 4 wherein the solvent is selected from the group consisting of aliphatic hydrocarbons having 5-20 carbon atoms, aromatic hydrocarbons having 6-20 carbon atoms and organic acid esters having 3-20 carbon atoms.

7. The process as defined in claim 1 wherein the hydrogen gas contains carbon monoxide.

8. The process as defined in claim 7 wherein carbon monoxide content in the hydrogen gap is between 0.1-90 mol %.

9. The process as defined in claim 7 wherein carbon monoxide content in the hydrogen gas is between 1 and 90 mol %.

10. The process as defined in claim 1 wherein the amount of the halide material employed is in the range of from $10^{-3}$ to 15 mol per 1 liter of a reaction solution.

11. The process as defined in claim 1 wherein said reaction is carried out in the presence of said catalyst comprising said component (a) and said component (b) and together with at least one promoter, said promoter being selected from the group consisting of metals having atomic weight of at least 6 and belonging to Groups Ia, IIa, IIIa, IVa, Va, Ib, IIb, Vb, VIb and VIIb of the Periodic Table, compounds of the metals and mixtures thereof.

12. The process as defined in claim 11 wherein the amount of said promoter employed is in the range of from $10^{-5}$ to 25% by weight on the basis of weight of a reaction solution.

13. The process as defined in claim 11 wherein said promoter is selected from the group consisting of fluorides, chlorides, bromides, iodides, sulfates, phosphates, organic acid salts and mixtures thereof.

14. The process as defined in claim 11 wherein said promoter is selected from the group consisting of lithium, potassium, barium and antimony and compounds of these metals.

15. The process as defined in claim 14 wherein said promoter is selected from the group consisting of fluorides, chlorides bromides, iodides, sulfates, phosphates, organic acid salts, and mixtures thereof.

16. The process as defined in any one of claims 10-12 or 1-9 wherein the reaction is carried out in a temperature of range 20°-500° C.

* * * * *